United States Patent
Yanke

(10) Patent No.: US 10,363,328 B2
(45) Date of Patent: Jul. 30, 2019

(54) ANTI-MICROBIAL CASH DRAWER

(71) Applicant: Richard D. Yanke, Burbank, CA (US)

(72) Inventor: Richard D. Yanke, Burbank, CA (US)

(73) Assignee: Richard D. Yanke, Burbank, CA (US)

( * ) Notice: Subject to any disclaimer, the term of this patent is extended or adjusted under 35 U.S.C. 154(b) by 232 days.

(21) Appl. No.: 15/296,151

(22) Filed: Oct. 18, 2016

(65) Prior Publication Data
US 2017/0035923 A1 Feb. 9, 2017

Related U.S. Application Data

(63) Continuation-in-part of application No. 14/691,631, filed on Apr. 21, 2015, now Pat. No. 9,498,551.
(Continued)

(51) Int. Cl.
*A61L 2/00* (2006.01)
*A61L 2/18* (2006.01)
(Continued)

(52) U.S. Cl.
CPC .............. *A61L 2/22* (2013.01); *A61L 2/00* (2013.01); *A61L 2/0082* (2013.01); *A61L 2/10* (2013.01);
(Continued)

(58) Field of Classification Search
CPC .................................. A61L 2/22; A47L 13/51
(Continued)

(56) References Cited

U.S. PATENT DOCUMENTS

2006/0003912 A1* 1/2006 Lindsay ............. A47L 13/16
510/267
2009/0159598 A1* 6/2009 Kuehneman ......... B65D 25/04
220/553
(Continued)

OTHER PUBLICATIONS

La, "Cleanwell All-Natural Hand Sanitizers & Soaps," Retrieved from www.saybaybee.com/all-natural-hand-sanitizers-soaps, Mar. 11, 2012 (Year: 2012).*

*Primary Examiner* — Kevin Joyner
*Assistant Examiner* — Holly M Mull
(74) *Attorney, Agent, or Firm* — Joseph F. Aceto, Esq.

(57) ABSTRACT

The invention relates to a system, methods and apparatus for efficiently and cost-effectively preventing the transfer of microbes, such as, for example, bacteria and viruses seamlessly during commercial transactions typically occurring at a full service check-out station in a large retail store. The invention further considers the application of the methods and apparatus in other industrial disciplines where, for example, medical equipment and surgical tools may be susceptible to cross-contamination of microbes. One preferred embodiment incorporates a slide able drawer within a cash box where currency is stored, taken, or added randomly over a period of time. Especially designed lamps allow for a rapid switching means to control the time period for activating or deactivating lamps, thus regulating UV exposure. Exposure time with UVC and the orientation of the UV lamps provides complete germicidal decontamination within seconds. A caddy containing natural botanical cleaning components, method of use and a microbe testing method are described to provide retail stores, hospitals and restaurants a highly efficient and cost-effective means to reduce or eliminate microbes on store surfaces.

7 Claims, 11 Drawing Sheets

Related U.S. Application Data

(60) Provisional application No. 61/983,385, filed on Apr. 23, 2014.

(51) Int. Cl.
  *A61L 2/22*   (2006.01)
  *A61L 2/28*   (2006.01)
  *A47L 13/51*  (2006.01)
  *A61L 2/10*   (2006.01)
  *C12Q 1/22*   (2006.01)
  *A61L 2/23*   (2006.01)
  *A61L 9/00*   (2006.01)

(52) U.S. Cl.
  CPC   *A61L 2/18* (2013.01); *A61L 2/23* (2013.01);
     *A61L 2/28* (2013.01); *A61L 9/00* (2013.01);
     *C12Q 1/22* (2013.01); *A61L 2202/122*
     (2013.01); *A61L 2202/15* (2013.01); *A61L 2202/16* (2013.01)

(58) Field of Classification Search
  USPC .......................................................... 422/24
  See application file for complete search history.

(56) References Cited

U.S. PATENT DOCUMENTS

| | | | |
|---|---|---|---|
| 2010/0203306 A1* | 8/2010 | Fingal | A47L 13/17 428/219 |
| 2012/0129950 A1* | 5/2012 | Macinga | A01N 31/02 514/738 |
| 2013/0198984 A1* | 8/2013 | Strandqvist | A47K 10/16 15/104.93 |
| 2016/0289059 A1 | 10/2016 | Nelson et al. | |

* cited by examiner

Panel A

Panel B

Panel C

Panel A

Panel B

Panel C

Panel A

Panel B

Panel A

Panel B

Panel C

Panel A

Panel B

Panel C

Panel D

Natural botanical disinfecting all-purpose spray cleaner

Natural botanical disinfecting wipes

Natural botanical spray hand sanitizer

Portable microbe detection device

Natural botanical sanitizer wipes

Natural botanical foaming hand sanitizer

ANTI-MICROBIAL CASH DRAWER

RELATED APPLICATIONS

This application is a continuation-in-part of U.S. Ser. No. 14/691,631, filed Apr. 21, 2015, which claims the benefit of U.S. Provisional Patent Application No. 61/983,385, filed Apr. 23, 2014, the disclosure of which is incorporated herein by reference in their entirety.

FIELDS OF THE INVENTION

The invention presented here relates to an ultraviolet sterilization system used for preventing the transfer of microbes, specifically in an integrated ultraviolet cash drawer. The design is used typically at a point of sale where a cash box is used to effect standard cash registration operations while seamlessly coupling ultraviolet sterilization on the cash transferred.

BACKGROUND

There are already a large number of devices described for effecting payment at a point of sale. Some have attempted to couple these devices with known anti-microbial or germicidal agents, however prior to the present invention any incorporation of these agents into cash registers or currency drawers involved commercially impractical designs and expensive manufacturing processes.

Related art includes two portable devices described in U.S. Pat. No. 4,786,812 issued on Nov. 22, 1988. This patent described for a hand-held device to sterilize a surface contaminated with mold, yeast or virus using ultraviolet (UV) lamps operating at a wavelength of 253.7 nanometers. U.S. Pat. No. 4,896,042 issued on Jan. 23, 1990 describes a two-piece device consisting of a hand-held unit with UV lamps for sterilization of surfaces and a base unit with a fan onto which the hand-held unit is secured for the sterilization of the surrounding atmosphere. Neither invention provides for or can ensure the complete decontamination of high-risk items, such as currency, during continual routine exchange of money as occurs in a check-out unit in department stores.

U.S. Pat. No. 6,753,536 describes the neutralization of chemical and biological threats using a confined drawer design that provides a contained decontamination of high-risk items such as money. The invention incorporates the use of a combination of germicidal and thermal tubes to neutralize chemical and/or biological agents. The ultraviolet lamps emit ultraviolet radiation, preferably UV-C at a wavelength of 253.7 nanometers with the heating tube generating air temperatures of at least 160° C.

In the retail industry, customers are highly susceptible to cross-contamination handling contaminated currency. Employees are constantly handling money which significantly increases their chances of infection. If employees and/or customers perceive a store and the company as begin unclean, the company brand and reputation will be affected.

None of the prior art inventions provide for or can safely and efficiently ensure complete decontamination of the currency exchanged during purchases as occurs in a check-out unit of a large retail store. Prior devices required long UV exposure times and cumbersome manipulation which delays the purchasing process normally occurring at a full service check-out station in a retail store.

A device for sterilizing currency, such as coins checks or other monetary exchange used and exchanged by the public, and that would allow an individual with little or no formal training to seamlessly and effectively decontaminate the currency. While completing routine exchanged related tasks such as would occur in a check-out line of a department store or large commercial facility would provide a useful means to control the communication of germs. Thus the present invention describes a device for sanitizing cash where there would be no change or alteration of normal operations, minimal integration into the current check-out stations, and no daily recurring costs or additional employee training is needed. Further, the present invention provides a means to use germicidal ultraviolet radiation to kill contaminants found on equipment in many various industries such as health care and in food preparatory where the spread of microbes among tools and bench-top equipment has become a problem for workers and consumers in the field.

SUMMARY

Banknotes, coins, and other forms of money have always been used in circulation as a medium of exchange especially circulating paper money. Individual paper currency will be in physical contact with multiple people and consequently become an inadvertent vector for the transmission of microbes in communities. This is especially true in large retail stores where patrons select their purchase items and then proceed to a central check-out station(s) to finalize the exchange using currency. As individual currency is exchanged through a check-out clerk and subsequent purchasers, the risk of communicating a plethora of microbial organisms increases through currency contact. Individuals, especially people with suppressed immune systems, are unnecessarily exposed to multiple diseases.

The present invention incorporates an ultraviolet sterilization system for safely and efficiently irradiating money at the point of currency transactions with ultraviolet light (UVC). In one embodiment, a cash drawer incorporates, in part, an outer casing configured to substantially enclose an inner volume, an inner container configured to receive a paper currency, and a series of electrical components designed to completely irradiate with ultraviolet light, specifically UVC, the target monies in an optimized time interval that allows continued addition and removal of currency during routine purchases and exchange of money.

A further embodiment includes design modifications for easy repair and maintenance. A modular design as described herein provides for a rapid and simple manufacturing process.

The present invention provides germicidal protection for full-service check-out stations in stores, in part, by retro fitting current cash drawers with a UV system that significantly reduces or eliminates the exchange of microbes occurring with the transfer of currency. This "real time" UV irradiation and currency exchange make the present invention useful in most retail stores and large commercial entities were currency is exchanged with the public.

A still further embodiment includes a caddy device for housing a kit providing germicidal protection. The caddy, together with the kit, provides consistent and complete germicidal protection in retail stores, hospital or restaurants where employees routinely clean the surfaces of tables, check-out stations or other surfaces in contact with people over the course of the day. The caddy has a series of specific portals on the top surface that directs the user to select the appropriate natural botanical disinfectant and ensures the proper selection of the towel and disposal based on a numbering system and color coding on the surface of the caddy.

A further method incorporates the use of the caddy device and kit components to provide a means to optimize the cleaning time and costs by sampling the surface with portable microbe detection device prior to cleaning. By sampling a surface over multiple cleaning events the portable microbe detection device provides a numerical value for the amount of microbes. Variations in the amount of microbes detected at specific cleaning sites within a retail store, hospital or restaurant determine, in part, whether the sites will continue to be cleaned at the same interval, cleaned over after an extended interval or cleaned over a shortened interval.

The embodiments of the present invention are shown in the drawings and summarized below. It is to be understood, however, that there is no intention to limit the invention to the forms described in the specification. One skilled in the art can recognize that there are numerous modifications that would embody the spirit and scope of the invention as expressed in the claims.

DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The device described in the present invention provides a system for significantly reducing or eliminating the exchange of microbes with the transfer of currency. One embodiment incorporates a currency box used in most commercial transactions or associated with cash registers used in large commercial entities such as retail stores. The box is equipped with a series of ultraviolet lamps (UVC) programed to irradiate the contents such as coins and notes. The UVC bulbs and electronic circuitry provide an efficient and commercially practical means to providing a germicidal sterilizer. The box is loaded with the currency. When the drawer is closed, a calculated dose of germicidal UVC energy is delivered automatically within the box, eliminating or significantly reducing the microbes. LED displays on the outer front face of the box provide the user with the system's status, including power, lamps, and lamp use. Other embodiments of the present invention include, but not limited to, a device and a disinfecting tool used in the healthcare industry and in the food preparatory industry where cutting boards and other instruments are readily sterilized.

Kits for maintaining a germ-free checkout station are also described which compliment the device in a system that provides a complete germ-free check out station. The kit includes, in part, a botanical disinfecting and sanitizing wipes and spray which further aid in the safety of the employee.

Overall UVC Germicidal and Antimicrobial System

Figure 1:
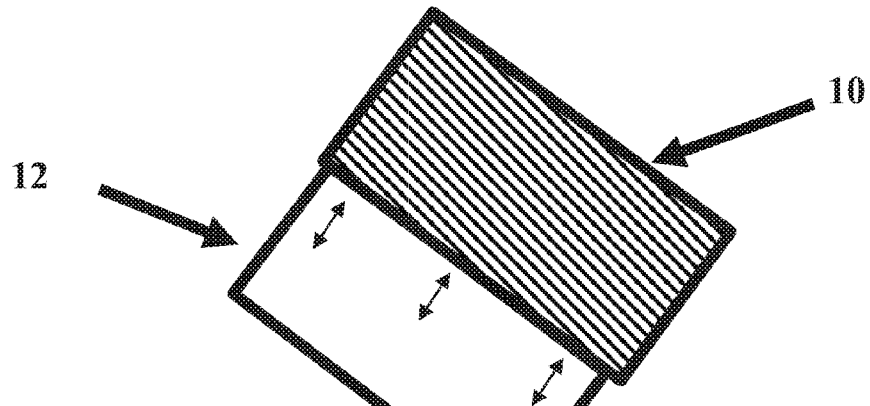
FIG. 1. Images of irradiation chamber design, Panel A single chamber area with no dividers, Panel B three chamber divider, and Panel C standard currency dividers.
Figure 1:
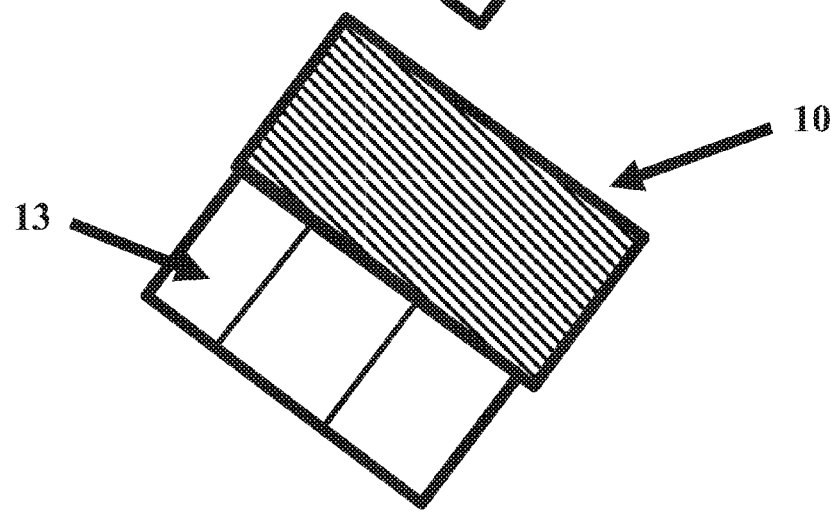
Figure 1:
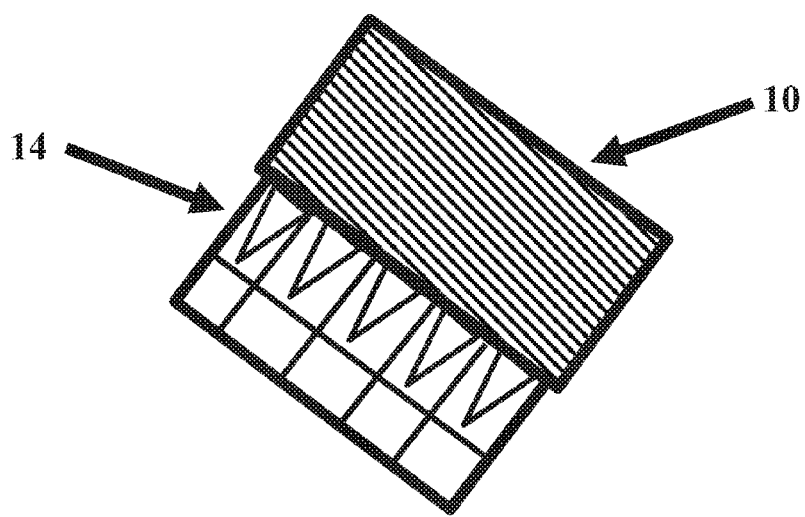

The PCB power circuit board and lamp circuit board is designed to lit in any type of sterilization system to sterilize a multitude of products, materials or tools. The target to be irradiated is contained within a closed unit. Typical contained units are shown in FIG. 1 where a drawer within the closed box provides easy access when pulled out. As illustrated, FIG. 1 Panel A depicts a sterilization unit having an outer box frame (10) with an inner draw (12) shown without dividers. FIG. 1 Panel B is the same outer box frame (10) and inner draw (13) with compartments. While any design for dividing the in draw is contemplated in the present invention, FIG. 1 Panel C depicts the most preferred design for the inner draw (14) having specific compartments for storing currencies of different denominations. Upon closing the inner drawer and activation of the system, the contents are exposed to a UVC source for a predetermined time period optimized to ensure complete elimination of any microbial activity on the surface of the target with the least amount of lamp usage.

Figure 2:
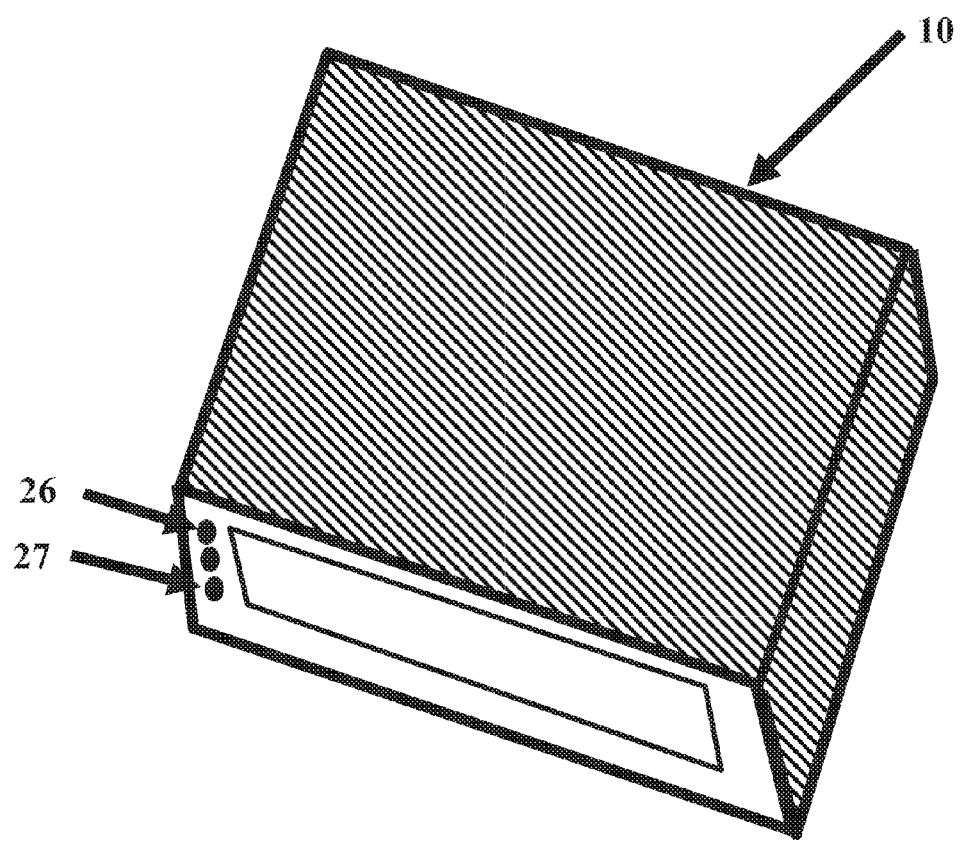
FIG. 2. Outer front face of box showing indicators LEDs, green indicates power on and blue indicates lamp on, located on the front face of the box.
Figure 3:
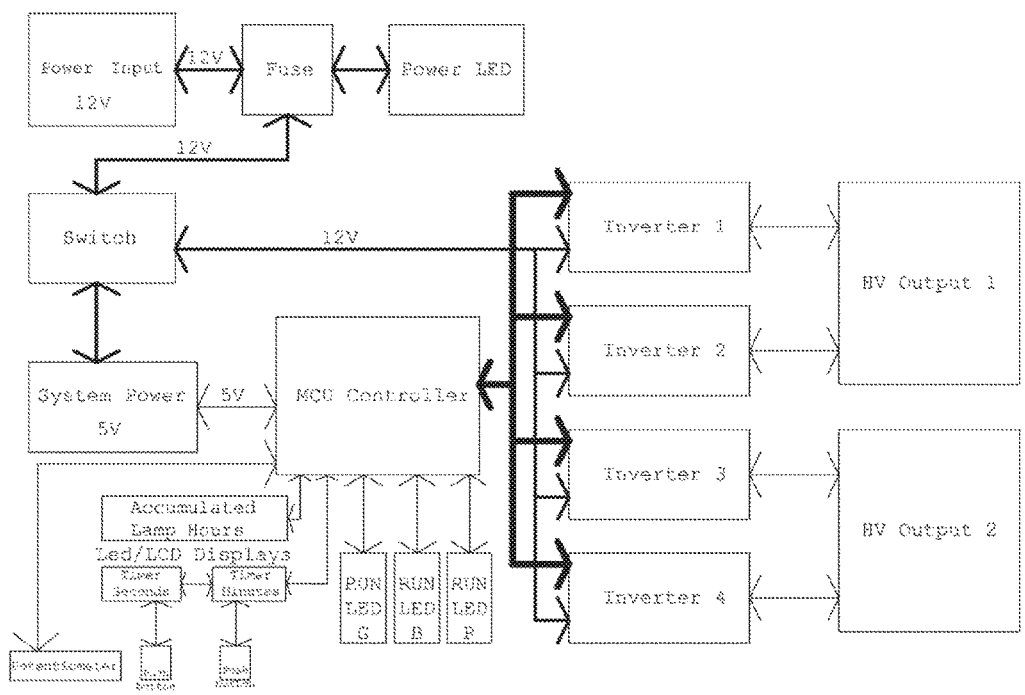
FIG. 3. Block diagram of main control board.

One embodiment of the present invention address the need for removing microbial activity on the surface of currency as it is being exchanged in commerce, typically the full-service check-out station at a retail store. The present invention utilizes, in part, the standard design of a cash box (10) having a currency drawer (but now incorporating a UVC irradiation system (FIG. 1, Panel C). On the left side of the front outer face of the outer cash box are green (26) and blue (27) LED indicator lights powered directly from the circuit board described herein (FIG. 2). Alternatively, a third red LED indicator light illuminates when the clock on the circuit board reaches 10,000 hours which functions to notify the user that the bulb is to be replaced. FIG. 3 provides a block diagram of the main control board, showing the interrelationships between the irradiation lamps and user indication LEDs. FIG. 3 incorporates the third red LED which alternatively can be used to assess the life of the UV bulbs.

Figure 4:
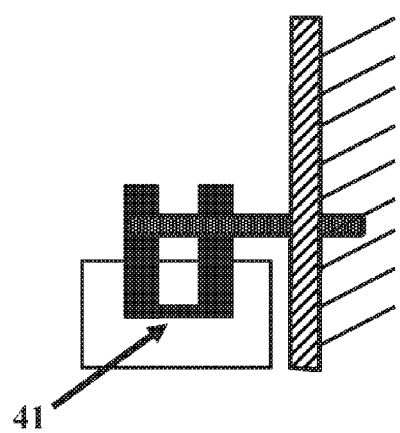
FIG. 4. Image of the micro switch design to accurately time the opening and closing of the drawer with the opening and closing of the UVC lamp. Panel A shows the V bend design. Panel B shows a modular design unit and Panel C shows the unit situated within outer box.
Figure 4:
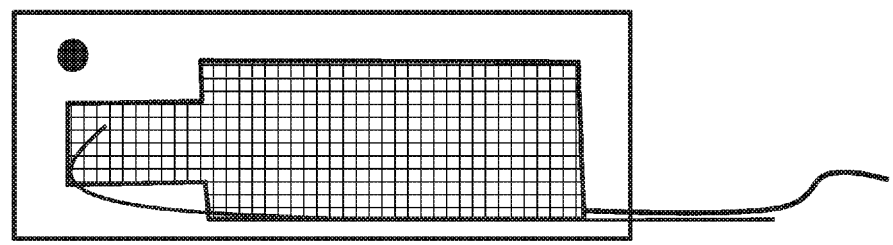
Figure 4:
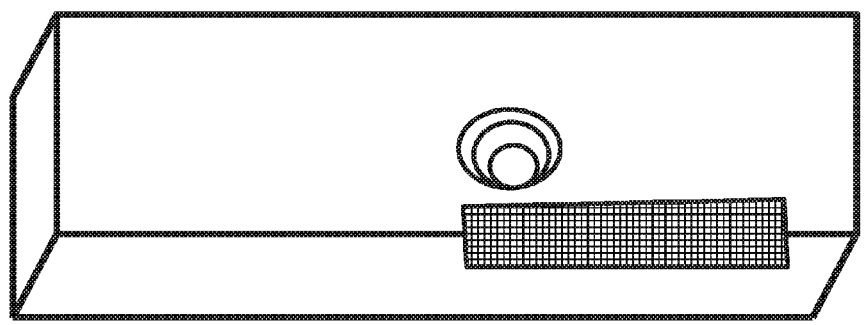

In one embodiment inside the outer box, a secondary micro switch is incorporated with the existing micro switch of the germicidal system through a specially designed connector (41). As shown in FIG. 4 Panel A, a V bend in the center keeps both arms of the switch connected as well as evenly separated. This insures smooth operation for the accuracy of the timing corresponding with the opening and closing of the germicidal chamber or cash drawer as well as the overall UVC operation.

In an alternate design, the LED indicator lights are positioned on the upper portion of the front face. A modular micro switch assembly is shown in FIG. 4, Panel B. As shown in FIG. 4, Panel C the assembly is easily mounted in the rear of the inner portion of the outer box with quick connectors.

Figure 5:
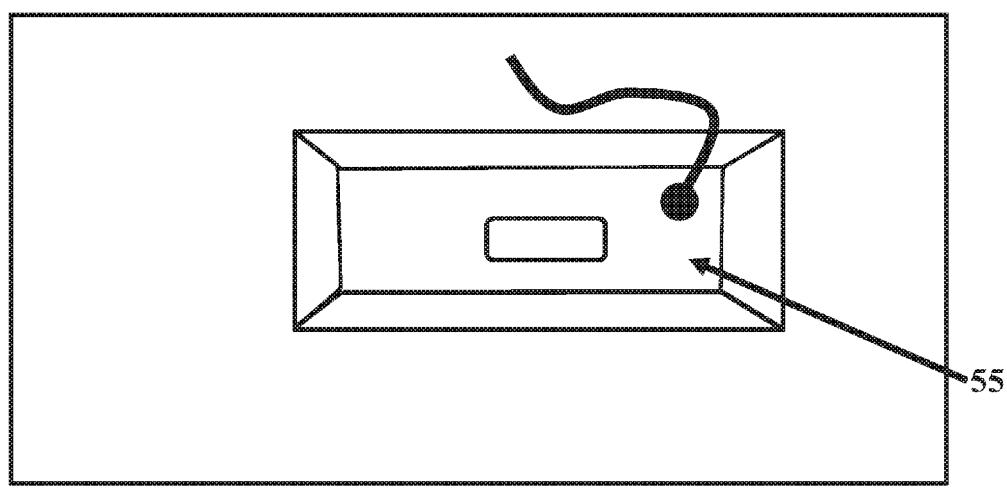
FIG. 5. Image of the recessed metal pocket housing the 12 volt power connection as well as the cash drawer POS interface.

Further the outside bottom of the outer box has a 2¾"× 1½×2" deep metal pocket (55) modified to contain a 12 volt power connection as well as the cash drawer POS interface. By recessing this pocket and locating the connectors within the pocket, the connectors are provided protection and the drawer will sit flat. (see FIG. 5)

Special quick release power plugs and connectors on the sterilization system as well an easily removable main PCB microprocessor circuit board and a PCB Ultraviolet-C lamp circuit board facilitate the efficient exchange of the parts of these components, allowing for cost-effective, quick and efficient service on site. The quick release plugs and connectors allow for rapid assembly and field repair.

The present invention considers all possible applications of the general embodiment of the present invention. Not only can it be applied to cash drawers, but replacement of the plastic cash drawer with a stainless steel mirrored polished drawer has applications in the medical and dental industry where rapid and easy sterilization of instruments or tools is needed to prevent infections.

Another application is in the food industry. One embodiment is a drawer without a bottom. The bottomless drawer is placed over cutting utensils and cutting boards to sterilize. An optimized exposure time to the UVC irradiation allows complete sterilization in-situ. Typical application would involve sterilization of a wood cutting board by simply placing the bottomless drawer over the target cutting board and exposing to UVC irradiation for a predetermined time period.

UVC—PCB Circuit Board Germicidial Sterilizer

FIG. 3 shows a block diagram of the main control board. All components are UL certified or are UL recognized components. A 2 pin male connector links the 12 volt DC input with a 3 amp fuse on circuit board. Another 2-Pin mate connects to 2 pin female connector attached to 18 gauge +− wires that connect to a 2.1 mm barrel power connector that installs in the bottom of the unit in the recessed pocket. The unit further contains (4) AC/DC high voltage rms transformers.

A microcomputer processor mounted on shock absorbing rubber grommets is incorporated to provide a custom program and a micro switch which functions in the assimilation of a one shot timer, controlling the transformers and LEDs. The blue LED UVC indicator light and the UVC germicidal lamps are switched on or off to indicate the status of the power or UV light, respectively. The processor also controls a potentiometer to supply the time required for the antimicrobial process. It is used to monitor, store and display the information and is set by two separate minute and second push button digital micro switches which when pressed will display the time that the UVC lamps will remain active, resulting in a much improved accuracy in regulating the amount of time the UV light is on, allowing for improved optimization of irradiation time intervals, and in standardizing the manufacture/product of multiple devices for a specific application. The processor is also used to monitor, store and display the information of the total accumulated time the UVC lamps have been active, thus providing an indication for replacement. The processor is responsible for monitoring and sending information to the red LED light when the life of the lamps has been exhausted and notifying the user to replace lamps. The LED green light on the front outside face of sterilization unit is constantly illuminated when power is applied to the unit. LED blue light on front outside face of the sterilization unit is illuminated only when power is applied from the micro switch, causing the microcomputer processor to engage the AC inverter to power the UVC bulbs and engage the timer, potentiometer and the LCD or LED readout. The LED (or LCD) panel on the outer front face of circuit board is controlled by the microcomputer processor which sends commands to the LED or LCD panel to display the accumulated time the UVC bulbs have been on. On the main PCB circuit board there are 2 brown male 11 pin output connectors. These connectors receive a set of custom designed 5000 k AC voltage silicone wires consisting of 4 red power and one white ground for AC voltage. Each set of cables has a brown female 11 pin connector on one end that connect to the circuit board and a white female 11 pin connector that connects to the Ultraviolet-C lamp circuit board.

The PCB Ultraviolet-C lamp Circuit Board

Figure 6:
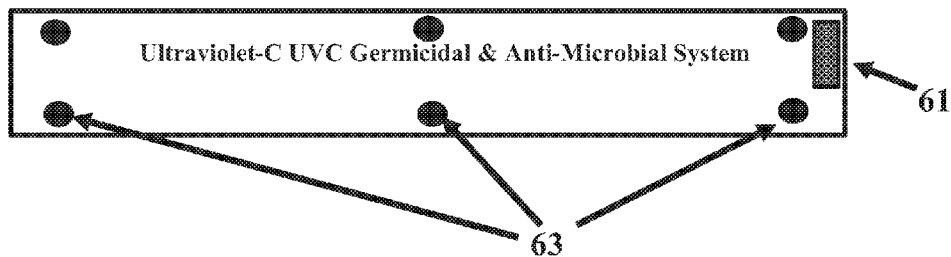
FIG. 6. Image of the ultraviolet-C circuit board and lamp mounted to the top portion of the inner surface of the outer box.

The PCB Ultraviolet-C (UVC) lamp and circuit board is shown in FIG. 6. FIG. 6 shows one embodiment where the board is 14 inch by 2⅞ inch with one white 11 pin male connector input (61). The 11 pin male connector is soldered to four traces that are designed for two germicidal UVC lamps, 5 watt, (5 mm×240 mm) having 253.7 nm wavelength with 2600 microwatts at 1 inch per $cm^2$. The lamps are staggered 2" left to right on the Ultraviolet-C lamp circuit board to provide complete coverage of the target area. These lamps are also soldered onto the Ultraviolet-C lamp circuit board so as to maintain a secure connection throughout their use. The lamps are designed to start quickly by using 1500 vrms to start and 900 vrms to run. This combination of power, size and characteristics of the lamp provides a unique feature to the lamps in the present invention, allowing them to start and reach its full power potential while killing 99.999% of germs within seconds instead of the minutes needed in the prior art. Thus the lamp allows faster service treatment on/off times when used and ensures complete irradiation during routine on/oil use.

The PCB lamp circuit board has 3 holes uniformly on each side of board (63). These holes allow a threaded brass insert attached to a steel pin which accompanies a rubber grommet to allow for shock absorption and for the circuit board to float above the attachment surface. A further embodiment of the PCB Lamp circuit board is a ⅜"×12" strip of hook and loop Velcro on back of the length of board making board simple to exchange when lamps need to be replaced.

Figure 7:
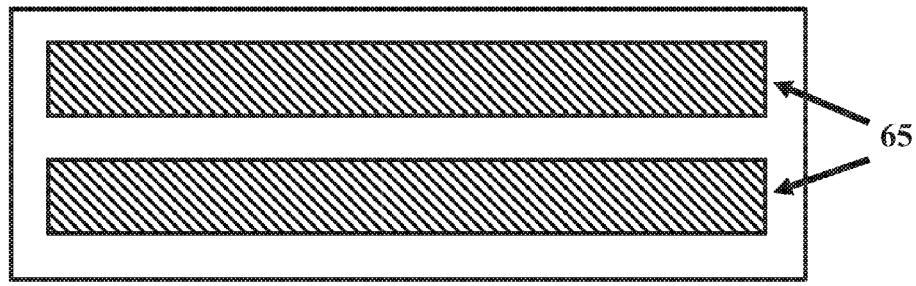
FIG. 7. Images of the modular design of the PCB lamp circuit board assembly. Panel A shows the UV-C circuit board and lamps mounted on an insulated platform. As shown in Panel B, a staggered pin orientation provides for simple installation.
Figure 7:
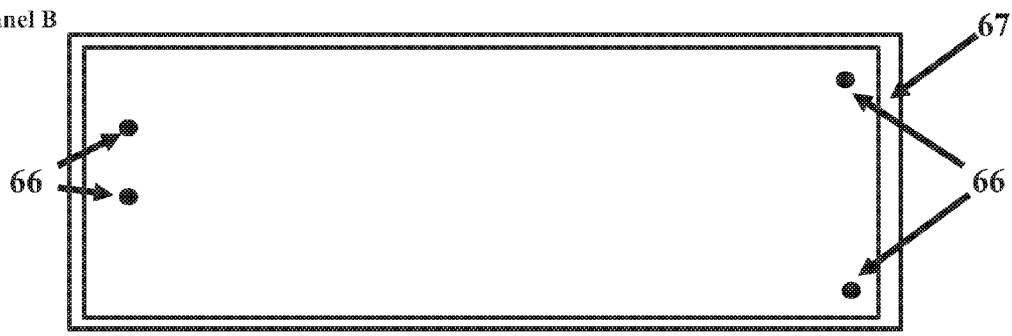
Figure 8:
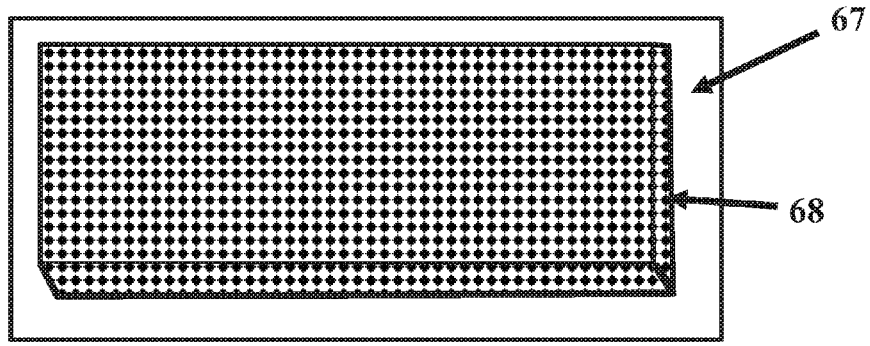
FIG. 8. Panel A shows an image of the protective screen inserted into position along the front and back 45 degree angle screen and platform edge. Panel B shows the modular circuit board and lamp with protective screen assembled on the inner surface of the top of the outer box. Panel C show an alternative design with standoff pins.
Figure 8:
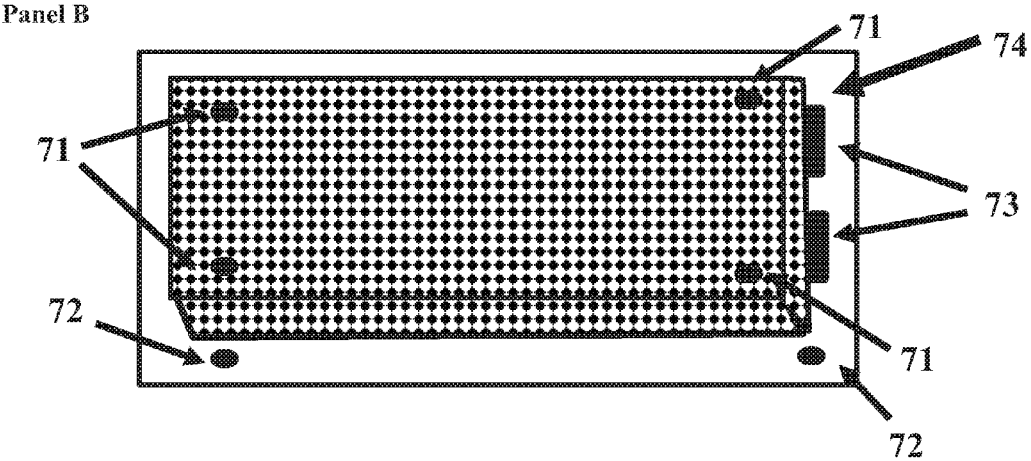
Figure 8:
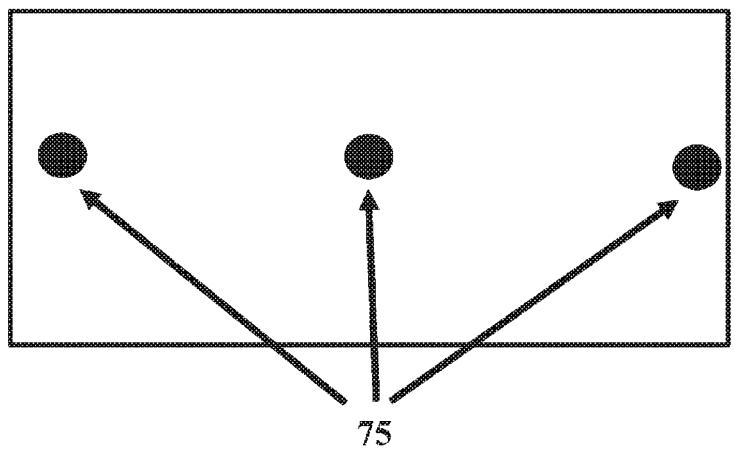

A further embodiment of the PCB Ultraviolet-C (UVC) lamp and circuit board is shown in FIG. 7. FIG. 7 Panel A shows a modular UVC lamp unit for assembly into a UV cash box. Two separate PCB lamp circuit board assemblies (65), each having two UV-C lamps are mounted on the circuit board. The PCB lamp circuit board assemblies (65) are easily mounted on an aluminum platform (67) having an insulated surface and using a staggered pin orientation (66) as shown in Panel B. An aluminum perforated protective screen (68) as described below covers the Ultraviolet-C (UVC) lamp and circuit board. The protective screen is inserted onto the aluminum plate (67) along the front and back 45 degree angle screen edge and a corresponding 45 degree angle edge of the aluminum platform as shown in FIG. 8 Panel A. Once assembled the modular lamp component is quickly and easily installed with 4 screws (71) onto a support platform (72) on the inner top surface of the outer box. The circuit board and lamp are connected to the unit through a two circuit hoard connectors (73) having a hold-down shield (74) as shown in FIG. 8 Panel B. Panel C depicts another embodiment which incorporates the modular design with standoff pins (75) in the center of the aluminum platform (67) to support the screen and allow for it to be screwed down.

The Aluminum Perforated Protective Screen

Figure 9:
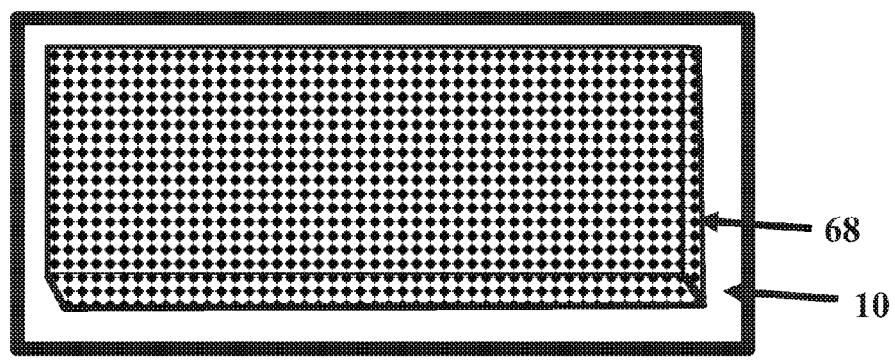
FIG. 9. Image of the aluminum protective screen shown on inner surface of the top side currency drawer FIG. 10. Insider view of the aluminum protective screen showing sides angled at 90 degrees with portions cut open for wire access and on the front and back edges a 45 degree angle.
Figure 10:
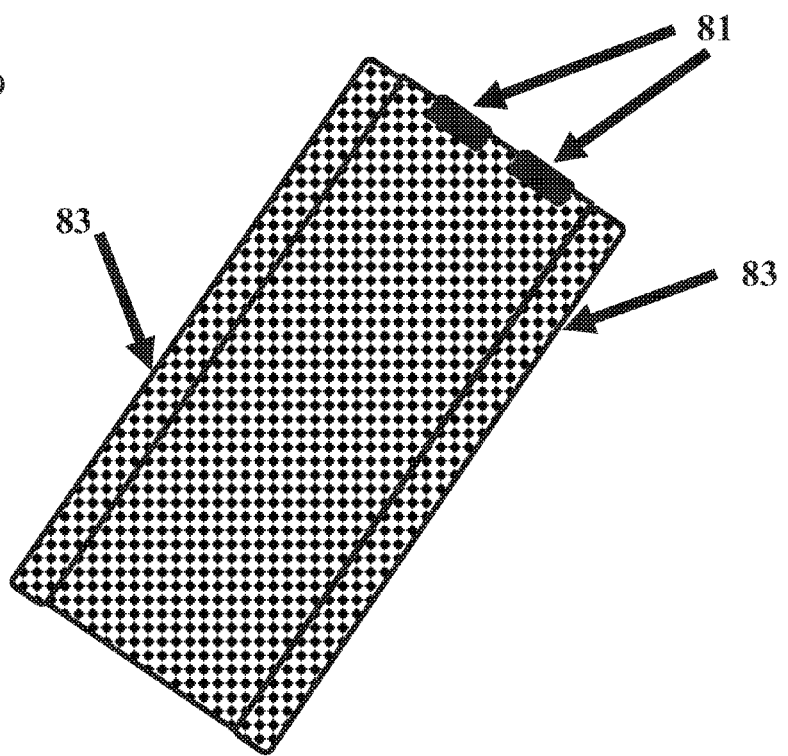

As shown in FIG. 9, a 15"×8" an aluminum perforated protective screen protects the boards from damage and allows the target, such as coins or paper notes, to be exposed to the generated radiation. FIG. 9 shows the outer box with the bottom side up and with the drawer removed. The aluminum perforated screen (68) is attached to the inner surface of the top side of the outer box (10). As shown in FIG. 10, the screen is angled at 90 degrees on each side with portions cut open for wire access (81) and on the front and back edges up, at a 45 degree angle so as to raise the center of the screen to provide a protective area for the PCB Lamp circuit board. The 45 degree angle also provides deflection for the drawer if it happens to be raised or the system is abused. The system is capable of preventing a high degree of abuse and will not allow the bulbs to break. If the bulbs do break, the screen will provide containment and will not allow the broken lamp to fall into the drawer. The perforation on the screen allows the 254.7 nm light waves to penetrate through and be effective in sterilizing the contents of the drawer. In addition, the screen is painted black on the back side as to not allow any reflection of the light wave so the fill strength of the light wave moves through the perforated protective screen.

Figure 11:
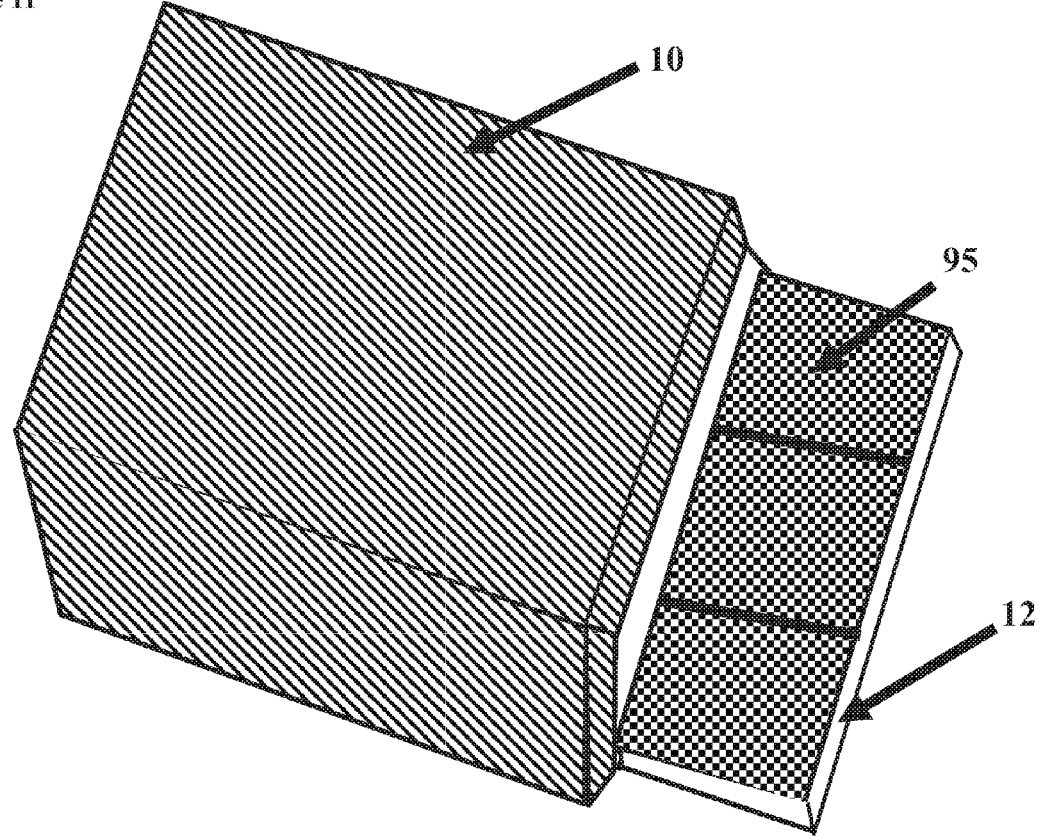
FIG. 11. Top view of an opened drawer modified for disinfecting medical equipment.

As discussed above, the present invention has applications in the healthcare industry (see FIG. 11). One embodiment is the use of the outside box (10) and drawer (12) in disinfecting medical instruments prior to use. Specially designed compartments enable complete exposure of the surface of each tool to the UV-C radiation, thereby ensuring uniform disinfection. To this end, stainless steel mirrored polished compartments allow light to be reflected from all interior drawer surfaces. A mesh platform (95) sits slightly above the bottom surface of the compartment. The mesh pattern is sufficiently porous as to allow UVC tight to reflect of the bottom drawer surface to irradiate the underside of the tool. FIG. 11 shows a typical medical sterilization drawer having three compartments for positioning medical and surgical tools for UV-C irradiation. Each compartment is fitted for a mesh platform as shown.

A further embodiment contemplated in the present invention is the incorporation of a small credit card size computer with WIFI capabilities. Together with a cell phone application to collect data on the status of the cash drawer (or other device of the present invention), individual cash drawers are monitored in real-time: For example, the application can assess the status of the power supply or information from the indicator lights. Information regarding the UV lamps relating to on/off time or time each lamp is on, record of the lifetime on the UVC bulbs to indicate replacement, the temperature inside the cash drawer, the number of times the cash drawer opens in a unit of time, detecting the cash drawer open time and assess. Thus if left open to long (theft or another problem), appropriate action can be quickly initiated. These all are set to be monitored without supervision and send a communication by e-mail to the responsible party as well as the owner, informing them that there is any type of problems with the drawer.

Sample Test

In order to further confirm the ability of the cash drawer to completely affect microbes and disinfect the surface of any currency transferred during the completion of a purchase or at the check-out station, three separate bills were randomly tested from two actively currency transacting stores, a restaurant and a pharmacy. Each selected bill was aseptically stored and transferred by sterile techniques prior to testing. Testing was completed by independently swabbing the surface of the collected bills before and after exposure to the UV-C cash drawer system described in the present invention. Petri dishes were incubated for 72 hours at 32° C. and then assessed for microbial growth on the agar.

Figure 12:
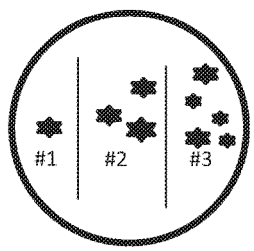
FIG. 12. Panels A and C are images of two petri dishes sampled from currency obtained from a restaurant and pharmacy, respectively. Each petri dish was inoculated from 3 different bills used in a typical transaction within the store and without exposing to the UV-C cash drawer system of the present invention. Panels B and D are images of petri dishes sampled from the same currency in Panel A and C, respectively, after disinfection using the UV-C in the cash drawer. Samples for each petri dish were obtained under aseptic conditions with each dish incubated for 72 hours at 32° C.
Figure 12:
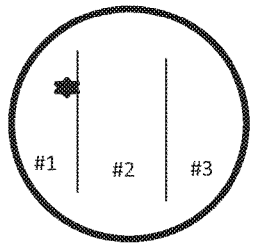
Figure 12:
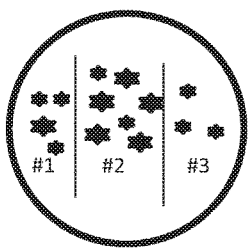
Figure 12:
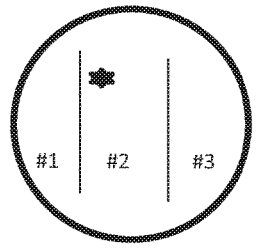

In the first experiment (FIG. 12, Panel A and B), currency exchanged from a fast-food restaurant was selected. Three bills were each independently swabbed to inoculate a sterile petri dish in three separate regions as shown. Panel A depicts growth in each region after 72 hours of incubation. While each bill had varying amounts of microbial growth, Panel A shows the presence of microbes growing on the petri dish in each region, representing their presence on the surface of the sampled bills. In Panel B, the same currency has now been disinfected using the UV-C cash drawer disinfection system of the present invention. Here, microbe growth has been significantly attenuated, if not completely inhibited, after exposure of the bills to the UV-C cash drawer system.

In the second experiment (FIG. 12, Panel C and D), currency exchanged from a pharmacy was selected. Again, three bills were each independently swabbed to inoculate a sterile petri dish in three separate regions. Panel C shows a significantly greater amount of infection in all three bills compared to the restaurant sample, but especially noteworthy is Panel D where the growth is again completely inhibited on all three samples after exposure to the UV-C cash drawer system.

Kit and System for a Complete Anti-Germicidal Protection System

In addition to the device described above, a complete system is disclosed herein for continued, long-term protection against microbes and other biological agents found and transmitted at most large commercial full-size check-out stations, such as those found at a department store or discount retail stores or protection against microbes on surfaces in retail stores, hospital and restaurants. The kit ensures all surfaces and employee/user hands are cleaned and surfaces monitored for a clean store environment. The kit includes, in part, natural botanical thymol sanitizing wipes, natural botanical thymol hand sanitizer, non-woven disinfecting towels (such as a blue/white striped non-woven towel made of 70% viscose and 30% polyester or blue spunlace non-woven towels made of 70% woodpulp and 30% polypropylene), and a natural botanical thymol disinfecting all-purpose spray cleaner (see FIG. 13).

A caddy device is described containing a natural botanical thymol disinfecting all-purpose spray cleaner (preferably a 16 oz spray bottle), a natural botanical thymol hand sanitizer (preferably a 4 oz spray bottle), rubber gloves (preferably 50 medium/large blue rubber gloves), natural botanical sanitizing wet wipes, and non-woven disinfecting towels (preferably a 50 count roll of blue/white striped non-woven towel made of 70% viscose and 30% polyester and blue spunlace non-woven towels made of 70% woodpulp and 30% polypropylene) for use in a specific number and color coded sequence of cleaning steps designate where each sections of the caddy is numbered and color coded, eliminating cleaning errors and minimize cleaning time within the store. As employees routinely clean surface areas exposed to contact from customers such as dining tables, check-our stations or other surfaces over the course of the day, improper technique by employees and inappropriate cleaners will not provide the consistency and level of germicidal cleaning needed for these surfaces. When used with the methods described herein, the caddy and kit provide a cleaning and testing system that ensures all surfaces and employee hands are clean and monitored regularly.

Figure 14:
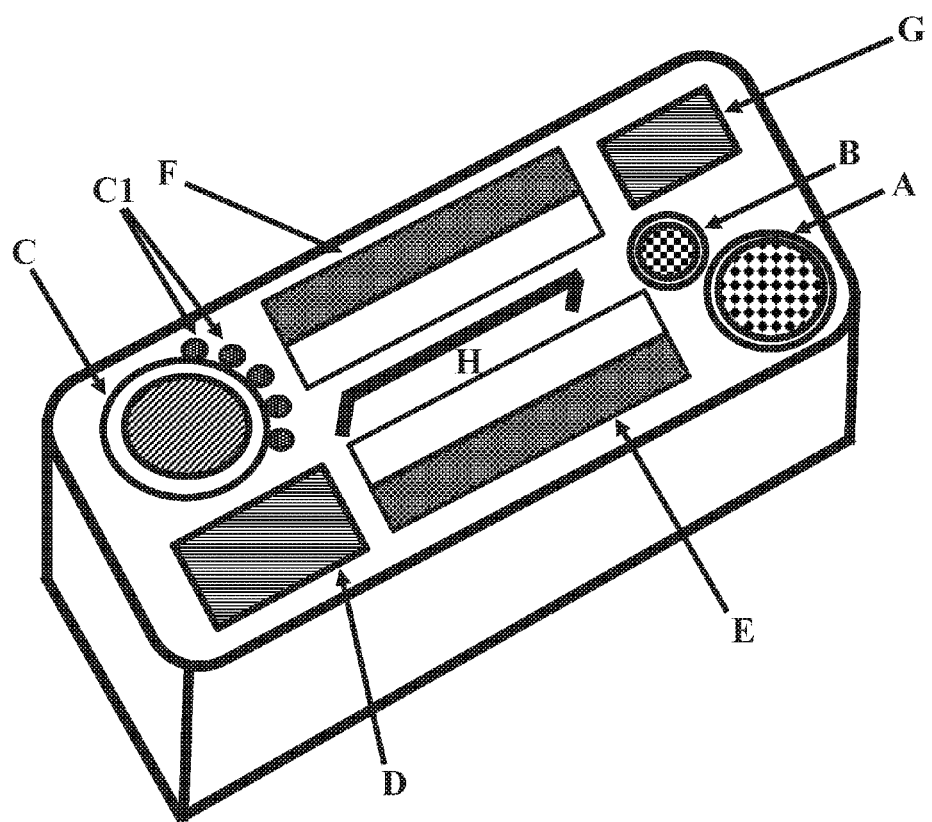
FIG. 14. Schematic view of the top surface of the caddy showing the relative positions of the specific portals.

As shown in FIG. 14, the caddy, in part, is a container with specifically numbered and color-coded portals on the surface designed to reduce user error and provide easy storage. These portals include a site for the botanical thymol disinfecting all-purpose spray cleaner (A); a site for the botanical thymol hand sanitizer (B); and a site for the thymol sanitizing wipes (C) and 5 smaller portals (C1) for test swabs used with the portable microbe detection device. The botanical thymol disinfecting all-purpose spray cleaner and hand sanitizer sites are located together in one section of the caddy surface so that the user associates this portion of the caddy with botanical thymol disinfecting agents. The portal for the botanical disinfecting all-purpose spray cleaner has a significantly larger diameter than the hand sanitizer to prevent user confusion as to which bottle is to be used. The site for the sanitizing wipes (C) is located on the opposite side of the caddy surface next to a compartment (D) for holding 50 medium/large rubber gloves. This region localizes user protective components and is color coded to ensure that the user associates this portion of the caddy to his/her protection. A compartment (E) has a lid and a slit in the side to hold a custom sized, 50 count roll, blue spunlace towel comprised of 70% woodpulp and 30% polypropylene. Compartment (F) also has a lid and a slit in the side to hold a custom sized 50 count roll, blue/white striped non-woven towel made of 70% viscose and 30% polyester, Compartment (G) is located in a separate color-coded region and represents the waste compartment for placing used wipes and gloves, reducing the potential of reusing the same wipe and reintroducing the microbes onto the cleaned surface. The container has a portable light-weight plastic polymer design with an easy carry handle (H) to allow for all the disinfectant components to be easily stored and transported when in use.

Accordingly when an employee or user cleans a dining table or other surface in a restaurant, hospital or retail store in his/her daily cleaning regime, the user carries the caddy to the table or surface to be cleaned and puts on a set of rubber gloves from the caddy (D). The user simply sprays the surface with the natural botanical disinfecting all-purpose spray cleaner (A). They can either let the spray dry on the table or wipe the surface with botanical non-woven towel from (E) or (F). The towels are preferably non-woven towels made of 70% viscose and 30% polyester for scrubbing surfaces or a blue spunlace towel containing 70% woodpulp and 30% polypropylene for drying surfaces. The user then disposes of the gloves and towel in the disposal portal (G). After cleaning is complete, the user sprays the botanical hand sanitizer on their hands from (B) and uses the sanitizing wet wipes (C) before proceeding to the next surface.

Figure 13:
FIG. 13. Image of the components for the kit of the present invention. The components includes natural botanical sanitizing wipes, foaming and spray hand sanitizer, disinfecting wipes, a disinfecting all-purpose spray cleaner and a portable microbe detection device.
Figure 13:
Figure 13:
Figure 13:
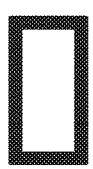
Figure 13:
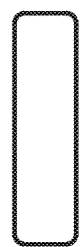
Figure 13:
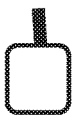

The caddy is also incorporated in a test method for optimizing the time and cost in maintaining a daily cleaning regime. Accordingly the caddy device and the cleaning components are incorporated into a series of routine surface cleaning as previously described. The surface is then monitored after each cleaning for microbe growth using a portable microbe detection device. Prior to each cleaning, each surface is sampled from a test swab (C1) systematically wiped across the targeted surface and counted using the portable microbe detection device (FIG. 13). The device will detect variations in the recurring microbe count on the surface prior to the next cleaning. Variations in the amount of microbes detected at specific cleaning surfaces in a retail store, hospital or restaurant determine, in part, whether these surfaces will continue to be routinely cleaned at the same interval, cleaned over an extended interval when little growth is detected or cleaned over a shortened interval when significant growth is detected between cleanings. By recording these changes over a period of time, a profile of microbe contamination is obtained. The user will then be able to increase the number of cleaning events on surfaces having higher microbe counts and reduce the number of cleaning events on surfaces that show no or significantly reduced microbe counts.

Most disinfectant wipes incorporate alcohols, aldehydes, oxidizing agents, phenolics, and quaternary ammonium compounds. Each has known properties and toxicities with varying safety standards. For example, bleach is commonly used to sanitize, especially in areas used by children. Bleach is a chemical irritant to the lungs and mucous membranes and is especially toxic to the individual who is diluting or cleaning the surface.

However the present invention considers a natural botanical alternative incorporated into the kit components, providing the safest work environment available for employees working at the store's full-service check-out station, on the dining surface in restaurants and for their customers. Natural botanical ingredients used in the formulation of the present invention include *Thymus vulgaris* oil or thymol (thyme oil which is a natural antimicrobial), citric acid (an antioxidant and environmentally benign cleaning agent), sodium decylglucosides hydroxypropyl sulfonate (a plant-based emulsifier derived from corn sugar and coconut oil), hydrolyzed oats (a skin conditioner), *Origanum vulgare* (oregano) oil (a natural essential oil fragrance), aloe barbadensis leaf (aloe vera, a natural emollient and skin conditioner), copper PCA (a skin conditioner and naturally occurring mineral found in human skin), Metrine (natural antimicrobial), *Cinnamomum zeylanicum* (cinnamon) an essential oil contains cinnamaldehyde which is a natural antimicrobial), sodium citrate (a natural pH balancer) and dihydrogen oxide (water).

The only known natural disinfectants are botanical disinfectants. Botanical disinfectants are known and proven to kill over 99.99% of bacteria, fungus and other microbes. They are applied without mixing, requiring no rinsing or wiping to remove. It can be used to sanitize such areas as a child care facility. It is most applicable in a work environment where an effective disinfectant is needed, yet the application must be safe for employees and other personnel who come in contact.

As a verification component of the kit, a portable microbe detection device is included with the kit in order to sample the individual check-out stations and monitor for the presence of microbes. While all detection devices known in the art are considered, the preferred device utilizes the detection of ATP. This is the simplest, fastest and most cost-effective rapid testing means for measuring mold, bacteria and other microbes.

The kit further contains information and instructions to optimize the use of the botanical disinfectant and a testing schedule for sampling with the portable microbe detection device.

The contents of the articles, patents, and patents applications and all other documents and electronically available information mentioned or cited herein, are hereby incorporated by reference in their entirety to the same extent as if each individual publication was specifically and individually indicated to be incorporated by reference.

The terms and expressions used herein have been used as terms of description and not of limitation, and there is no intention in the use of such terms of excluding any equivalents of the features shown and described or portions thereof. It is recognized that various modification are possible within the scope of the invention claimed. Thus, it should be understood that although the present invention has been specifically disclosed by preferred embodiments and other features, modification and variation of the invention embodied therein herein disclosed may be used by those skilled in the art, and that such modification and variations are considered to be within the scope of this invention.

I claim:

1. A caddy for providing germicidal protection on surfaces in retail stores, hospitals and restaurants comprising:
   a. a container composed of a plastic polymer having a handle and portals on a top surface;
   b. a botanical thymol disinfecting all-purpose spray cleaner comprising Metrine;
   c. a botanical thymol hand sanitizer;
   d. botanical thymol wet wipes;
   e. at least 5 test swabs;
   f. a non-woven towel for scrubbing the surface; and
   g. a spunlace towel for drying the surface, where the portals are numbered and color-coded for storing components b, c, d, e, and f when cleaning or testing retail store, hospital and restaurant surfaces.

2. The caddy of claim 1 wherein the botanical thymol disinfecting all-purpose spray cleaner is a 16 oz spray bottle of botanical thymol disinfectant.

3. The caddy of claim 1 wherein the botanical thymol hand sanitizer is 4 oz spray bottle of botanical thymol hand sanitizer.

4. The caddy of claim 1 where the non-woven towel for scrubbing contains 70% viscose and 30% polyester.

5. The caddy of claim 1 where the spunlace towel contains 70% woodpulp and 30% polyester.

6. The caddy of claim 1 wherein the natural botanical thymol disinfecting all-purpose spray cleaner further contains *Thymus vulgaris* oil, citric acid, sodium decylglucosides hydroxypropyl sulfonate, hydrolyzed oats, *Origanum vulgare* oil, aloe barbadensis leaf, copper PCA, *Cinnamomum zeylanicum*, sodium citrate, and dihydrogen oxide.

7. The caddy of claim 1 wherein the test swabs are disposable swabs for use with a portable microbe detection device.

* * * * *